US006528700B1

United States Patent
(12) United States Patent
Baszczynski et al.

(10) Patent No.: US 6,528,700 B1
(45) Date of Patent: Mar. 4, 2003

(54) TARGETED MANIPULATION OF GENES IN PLANTS

(75) Inventors: Christopher L. Baszczynski, Urbandale, IA (US); Benjamin A. Bowen, Des Moines, IA (US); John H. Duesing, West Des Moines, IA (US); David J. Peterson, Ames, IA (US); Laura A. Tagliani, Ankeny, IA (US); Tong Zhu, Johnston, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/193,612

(22) Filed: Nov. 17, 1998

Related U.S. Application Data

(60) Provisional application No. 60/098,235, filed on Aug. 28, 1998, and provisional application No. 60/065,628, filed on Nov. 18, 1997.

(51) Int. Cl.[7] .......................... C12N 15/82; C12N 15/00

(52) U.S. Cl. ........................... 800/278; 435/6; 435/440; 435/468; 800/290; 800/300

(58) Field of Search ................................ 435/69.1, 440, 435/468, 410, 419, 320.1; 800/278, 285, 290, 291, 295, 300; 436/6

(56) References Cited

U.S. PATENT DOCUMENTS

| | | | | |
|---|---|---|---|---|
| 5,013,659 | A | | 5/1991 | Bedbrook et al. |
| 5,331,107 | A | * | 7/1994 | Anderson ................ 800/300.1 |
| 5,565,350 | A | | 10/1996 | Kmiec |
| 5,731,181 | A | | 3/1998 | Kmiec |
| 5,795,972 | A | | 8/1998 | Kmiec |
| 6,040,497 | A | | 3/2000 | Spencer et al. |
| 6,225,114 | B1 | | 5/2001 | Eichholtz et al. |

FOREIGN PATENT DOCUMENTS

| | | |
|---|---|---|
| WO | WO 92/17484 | 10/1992 |
| WO | WO 95/15972 | 6/1995 |
| WO | WO 97/04103 | 2/1997 |
| WO | WO 97/48714 | 12/1997 |
| WO | WO 98/54330 | 12/1998 |
| WO | WO 99/07865 | 2/1999 |
| WO | WO 99/23202 | 5/1999 |

OTHER PUBLICATIONS

Gherzi, R., et al., "Human Tenascin Gene: Structure of the 5'–Region, Identification, and Characterization of the Transcription Regulatory Sequences," 1995, *Journal of Biological Chemistry*, pp. 3429–3434, vol. 270(7).

Meisenberg, G., et al., "Introduction to Genetic Diseases," *Principals of Medical Biochemistry*, 1998, pp. 168–169, Mosby, St. Louis.

Perbal, B., "A Practical Guide to Molecular Cloning" 1988, pp.685–686, John Wiley and Sons, New York.

Albert et al., Site–Specific Integration of DNA into Wild –Type and Mutant 1ox Sites Placed in the Plant Genome, The Plant Journal, 1995, pp. 649–659, vol. 7(4), Plant Gene Expression Center, Albany, CA, USA.

Narasimhulu et al., Early Transcription of Agrobacterium T–DNA Genes in Tobacco and Maize, The Plant Cell, May 1996, pp. 873–886, vol. 8, American Society of Plant Physiologists.

Kmiec, *Genetic Manipulation in Mammalian Cells Using an RNA/DNA Chimeric Oligonucleotide*, Advanced Drug Delivery Reviews, 1995, pp. 333–340, vol. 17, Elsevier Science.

Yoon et al., *Targeted Gene Correction of Episomal DNA in Mammalian Cells Mediated by a Chimeric RNA/DNA Oligonucleotide*, Proc. Natl. Acad. Sci. USA, Mar. 1996, pp. 2071–2076, vol. 93, Genetics.

* cited by examiner

*Primary Examiner*—Sean McGarry
(74) *Attorney, Agent, or Firm*—Alston & Bird LLP

(57) ABSTRACT

Methods and compositions for altering a nucleotide sequence of interest in a plant is provided. The method involves introducing a chimeric oligonucleotide into a RNA residues with intervening DNA residues. The RNA blocks are homologous to a plant nucleotide sequence. The chimeric oligonucleotide is capable of folding to form a duplex oligonucleotide. The chimeric oligonucleotide is maintained within the nucleus of the plant whereby the alteration is introduced into the target sequences of the plant genome.

32 Claims, 13 Drawing Sheets

CHIMERIC OLIGONUCLEOTIDE

GGGGAATGCTGGAATCGCAATGCGGTCCTTGACAGCAGCTGTTTTTacagcugcugucAAGGACCgcauuGCGATTccagcauuccccGCGCGTTTTCGCGC TWO NUCLEOTIDE MODIFICATIONS (UNDERLINED) AT EACH OF TWO AMINO ACID TARGETS (BOLD) IN MAIZE EPSPS GENE; RNA RESIDUES BETWEEN TWO AMINO ACID TARGETS.

FIG. 1(a)

ACTIVE OLIGONUCLEOTIDE CONFORMATION

```
 TGCGCG-ccccuuacgaccTTAGCGuuacgCCAGGAAcugucgucgacaT
T                                                  T
T                                                  T
 TCGCGC GGGGAATGCTGGAATCGCAATGCGGTCCTTGACAGCAGCTGTT
        GlyAsnAlaGlyIleAlaMetArgSerLeuThrAlaAlaVal
```

TWO NUCLEOTIDE MODIFICATIONS (UNDERLINED) AT EACH OF TWO AMINO ACID TARGETS (BOLD) IN MAIZE EPSPS GENE; RNA RESIDUES BETWEEN TWO AMINO ACID TARGETS.

FIG. 1(b)

CHIMERIC OLIGONUCLEOTIDE

GGAATGCTGGAATTGCAATGCGGTCATTGACAGCAGTTTTcugcugucaaTGACCgcauugCAATTccagcauuccGCGCGTTTTCGCGC ONE NUCLEOTIDE MODIFICATION (UNDERLINED) AT EACH OF TWO AMINO ACID TARGETS (BOLD) IN MAIZE EPSPS GENE; RNA RESIDUES BETWEEN TWO AMINO ACID TARGETS.

FIG. 2(a)

ACTIVE OLIGONUCLEOTIDE CONFORMATION

```
 TGCGCG-ccuuacgaccTTAACguuacgCCAGTaacugucgucT
T                                            T
T                                            T
 TCGCGC GGAATGCTGGAATTGCAATGCGGTCATTGACAGCAGT
          AsnAlaGlyIleAlaMetArgSerLeuThrAla
```

ONE NUCLEOTIDE MODIFICATION (UNDERLINED) AT EACH OF TWO AMINO ACID TARGETS (BOLD) IN MAIZE EPSPS GENE; RNA RESIDUES BETWEEN TWO AMINO ACID TARGETS.

FIG. 2(b)

CHIMERIC OLIGONUCLEOTIDE

GGGGAATGCTGGAATCGCAATGCGGTCCTTGACAGCAGCTGTTTTTacagcugcugucAAGGACCGCATTGCGATTccagcauuccccGCGCGTTTTCGCGC TWO NUCLEOTIDE MODIFICATIONS (UNDERLINED) AT EACH OF TWO AMINO ACID TARGETS (BOLD) IN MAIZE EPSPS GENE; DNA RESIDUES BETWEEN TWO AMINO ACID TARGETS.

FIG. 3(a)

ACTIVE OLIGONUCLEOTIDE CONFORMATION

```
 TGCGCG-ccuuacgaccTTAACGTTACGCCAGTaacugucgucT
T                                            T
T                                            T
 TCGCGC GGAATGCTGGAATTGCAATGCGGTCATTGACAGCAGT
          AsnAlaGlyIleAlaMetArgSerLeuThrAla
```

TWO NUCLEOTIDE MODIFICATIONS (UNDERLINED) AT EACH OF TWO AMINO ACID TARGETS (BOLD) IN MAIZE EPSPS GENE; DNA RESIDUES BETWEEN TWO AMINO ACID TARGETS.

FIG. 3(b)

CHIMERIC OLIGONUCLEOTIDE

5'GGAATGCTGGAATTGCAATGCGGTCATTGACAGCAGTTTTcugcugucaaTGACCGCATTGCAATTccagcauuccGCGCGTTTTCGCGC ONE NUCLEOTIDE MODIFICATION (UNDERLINED) AT EACH OF TWO AMINO ACID TARGETS (BOLD) IN MAIZE EPSPS GENE; DNA RESIDUES BETWEEN TWO AMINO ACID TARGETS.

FIG. 4(a)

ACTIVE OLIGONUCLEOTIDE CONFORMATION

```
 TGCGCG-ccuuacgaccTTAACGTTACGCCAGTaacugucgucT
T                                            T
T                                            T
 TCGCGC GGAATGCTGGAATTGCAATGCGGTCATTGACAGCAGT
          AsnAlaGlyIleAlaMetArgSerLeuThrAla
```

ONE NUCLEOTIDE MODIFICATION (UNDERLINED) AT EACH OF TWO AMINO ACID TARGETS (BOLD) IN MAIZE EPSPS GENE; DNA RESIDUES BETWEEN TWO AMINO ACID TARGETS.

FIG. 4(b)

CHIMERIC OLIGONUCLEOTIDE

GGGGAATGCTGGAATCGCAATGCGGTCCTTGACAGCAGCTGTTTTacagcugcugucaaggaccgcauuGCGATTccagcauuccccGCGCGTTTTCGCGC TWO NUCLEOTIDE MODIFICATIONS (UNDERLINED) AT EACH OF TWO AMINO ACID TARGETS (BOLD) IN MAIZE EPSPS GENE; FIRST TARGET REGION WITHIN DNA, SECOND TARGET REGION WTHIN RNA.

FIG. 5(a)

ACTIVE OLIGONUCLEOTIDE CONFORMATION

```
 TGCGCG-ccccuuacgaccTTAGCGuuacgccaggaacugucgucgacaT
T                                                   T
T                                                   T
 TCGCGC GGGGAATGCTGGAATCGCAATGCGGTCCTTGACAGCAGCTGTT
          GlyAsnAlaGlyIleAlaMetArgSerLeuThrAlaAlaVal
```

TWO NUCLEOTIDE MODIFICATIONS (UNDERLINED) AT EACH OF TWO AMINO ACID TARGETS (BOLD) IN MAIZE EPSPS GENE; FIRST TARGET REGION WITHIN DNA, SECOND TARGET REGION WTHIN RNA.

FIG. 5(b)

CHIMERIC OLIGONUCLEOTIDE

5'GGAATGCTGGAATTGCAATGCGGTCATTGACAGTTTTcugucaaugaccgcauugCAATTccagcauuccGCGCGTTTTCGCGC ONE NUCLEOTIDE MODIFICATION (UNDERLINED) AT EACH OF TWO AMINO ACID TARGETS (BOLD) IN MAIZE EPSPS GENE; FIRST TARGET REGION WITHIN DNA, SECOND TARGET REGION WITHIN RNA.

FIG. 6(a)

ACTIVE OLIGONUCLEOTIDE CONFORMATION

```
 TGCGCG-ccuuacgaccTTAACguuacgccaguaacugucT
T                                         T
T                                         T
 TCGCGC GGAATGCTGGAATTGCAATGCGGTCATTGACAGT
          AsnAlaGlyIleAlaMetArgSerLeu
```

ONE NUCLEOTIDE MODIFICATION (UNDERLINED) AT EACH OF TWO AMINO ACID TARGETS (BOLD) IN MAIZE EPSPS GENE; FIRST TARGET REGION WITHIN DNA, SECOND TARGET REGION WITHIN RNA.

FIG. 6(b)

CHIMERIC OLIGONUCLEOTIDE

GGGGAATGCTGGAATCGCAATGCGGTCCTTGACAGCAGCTGTTTTacagcugcugucAAGGACCgcauugcgattccagcauuccccGCGCGTTTTCGCGC TWO NUCLEOTIDE MODIFICATIONS (UNDERLINED) AT EACH OF TWO AMINO ACID TARGETS (BOLD) IN MAIZE EPSPS GENE; FIRST TARGET REGION WITHIN RNA, SECOND REGION WITHIN DNA.

FIG. 7(a)

ACTIVE OLIGONUCLEOTIDE CONFORMATION

```
 TGCGCG-ccccuuacgaccttagcguuacgCCAGGAAcugucgucgacaT
T                                                  T
T                                                  T
 TCGCGC GGGGAATGCTGGAATCGCAATGCGGTCCTTGACAGCAGCTGTT
        GlyAsnAlaGlyIleAlaMetArgSerLeuThrAlaAlaVal
```

TWO NUCLEOTIDE MODIFICATIONS (UNDERLINED) AT EACH OF TWO AMINO ACID TARGETS (BOLD) IN MAIZE EPSPS GENE; FIRST TARGET REGION WITHIN RNA, SECOND REGION WITHIN DNA.

FIG. 7(b)

CHIMERIC OLIGONUCLEOTIDE

5'GGAATGCTGGAATTGCAATGCGGTCATTGACAGTTTTcugucaaugaccgcauugCAATTccagcauuccGCGCGTTTTCGCGC ONE NUCLEOTIDE MODIFICATION (UNDERLINED) AT EACH OF TWO AMINO ACID TARGETS (BOLD) IN MAIZE EPSPS GENE; FIRST TARGET REGION WITHIN RNA, SECOND TARGET REGION WITHIN DNA.

FIG. 8(a)

ACTIVE OLIGONUCLEOTIDE CONFORMATION

```
 TGCGCG-ccuuacgaccttaacguuacgCCAGUaacugucT
T                                         T
T                                         T
 TCGCGC GGAATGCTGGAATTGCAATGCGGTCATTGACAGT
          AsnAlaGlyIleAlaMetArgSerLeu
```

ONE NUCLEOTIDE MODIFICATION (UNDERLINED) AT EACH OF TWO AMINO ACID TARGETS (BOLD) IN MAIZE EPSPS GENE; FIRST TARGET REGION WITHIN RNA, SECOND TARGET REGION WITHIN DNA.

FIG. 8(b)

CHIMERIC OLIGONUCLEOTIDE

5'GGAATGCTGGAATTGCAATGCGGCCTTTTggccgcauugCAATTccagcauuccGCGCGTTTTCGCGC

ONE NUCLEOTIDE MODIFICATION (UNDERLINED) AT ONE AMINO ACID TARGET (BOLD).

FIG. 9(a)

ACTIVE OLIGONUCLEOTIDE CONFORMATION

```
 TGCGCG-ccuuacgaccTTAACguuacgccggT
T                                 T
T                                 T
 TCGCGC GGAATGCTGGAATTGCAATGCGGCCT
          AsnAlaGlyIleAlaMetArgPro
```

ONE NUCLEOTIDE MODIFICATION (UNDERLINED) AT ONE AMINO ACID TARGET (BOLD).

FIG. 9(b)

CHIMERIC OLIGONUCLEOTIDE

5'ACTGCAATGCGGTCATTGACAGCAGTTTTcugcugucaaTGACCgcauugcaguGCGCGTTTTCGCGC

ONE NUCLEOTIDE MODIFICATION (UNDERLINED) AT ONE AMINO ACID TARGET (BOLD).

FIG. 10(a)

ACTIVE OLIGONUCLEOTIDE CONFORMATION

```
 TGCGCG-ugacguuacgCCAGTaacugucgucT
T                                 T
T                                 T
 TCGCGC ACTGCAATGCGGTCATTGACAGCAGT
        ThrAlaMetArgSerLeuThrAla
```

ONE NUCLEOTIDE MODIFICATION (UNDERLINED) AT ONE AMINO ACID TARGET (BOLD).

FIG. 10(b)

CHIMERIC OLIGONUCLEOTIDE
(SINGLE MODIFICATION: Ser=>Asn BEING MADE)

5'CTATGATCCCTAATGGTGGGGCTTTTTTTaaagccccacCATTAgggaucauagGCGCGTTTTCGCGC

FIG. 11(a)

ACTIVE OLIGONUCLEOTIDE CONFORMATION

```
 TGCGCG-gauacuagggATTACcaccccgaaaT
T                                 T
T                                 T
 TCGCGC CTATGATCCCTAATGGTGGGGCTTTT
        5'MetIleProAsnGlyGlyAla
```

FIG. 11(b)

CHIMERIC OLIGONUCLEOTIDE
(SINGLE MODIFICATION: Pro=>Ala BEING MADE)

5'ACGGGACAGGTGGCGCGACGCATGATTTTtcaugcgucgCGCCAccugucccguGCGCGTTTTCGCGC

FIG. 12(a)

ACTIVE OLIGONUCLEOTIDE CONFORMATION

```
 TGCGCG-ugcccuguccACCGCgcugcguactT
T                                 T
T                                 T
 TCGCGC ACGGGACAGGTGGCGCGACGCATGAT
      5'ThrGlyGlnValAlaArgArgMet
```

FIG. 12(b)

CHIMERIC OLIGONUCLEOTIDE
(SINGLE MODIFICATION: *Ter*=>Tyr BEING MADE)

5'GACGCAGATCTACGTACCATCGTCCTTTTggacgaugguACGTAgaucugcgucGCGCGTTTTCGCGC

FIG. 13(a)

ACTIVE OLIGONUCLEOTIDE CONFORMATION

```
 TGCGCG-cugcgucuagATGCAugguagcaggT
T                                 T
T                                 T
 TCGCGC GACGCAGATCTACGTACCATCGTCCT
       5'ThrGlnIleTyrValProSerSer
```

FIG. 13(b)

TARGETED MANIPULATION OF GENES IN PLANTS

CROSS-REFERENCE TO RELATED APPLICATIONS

This application claims the benefit of U.S. application Ser. No. 60/098,235, filed Aug. 28, 1998, and U.S. application Ser. No. 60/065,628, filed Nov. 18, 1997, both of which are herein incorporated by reference.

FIELD OF INVENTION

The present invention is drawn to the genetic modification of higher plants using chimeric RNA/DNA oligonucleotides.

BACKGROUND OF THE INVENTION

Because of the complex organization and metabolic compartmentation in higher plants, many molecular tools have to be combined to successfully genetically manipulate a plant. At the present time, directed changes require a transformation system, a suitable gene, a promoter sequence capable of driving expression of the gene, effective targeting signals to direct the expression product to the correct destination in the cell, and often other regulatory elements.

There are many published systems for the transformation of plant cells. However, there remain drawbacks to each of the systems. For example, *Agrobacterium tumefaciens*gene transfer is widely used for creating transgenic plants, however, in some plants making a successful transformation utilizing the Agrobacterium system is difficult. Other systems include particle bombardment, viral vectors, protoplast transformation via polyethylene glycol or electroporation, microinjection of DNA into protoplast, and macroinjection of DNA. Of these, the most successful method to date is particle bombardment of embryogenic calli for developing embryos. Even this transformation system suffers from a lack of genomic targeting control for insertion of the foreign gene. In addition, bombardment results in multiple insertions of the foreign gene into the plant genome.

Any transformation system in plants, must deal with the problems of cosuppression which occurs when endogenous genes are down-regulated by expression of homologous sense transcripts. Expression of chimeric gene constructs have led to the down-regulation of genes in transgenic plants, however the effects of cosuppression are variable, and the underlying mechanisms remain unclear.

Site-directed manipulation of chromosomal genes has become the method of choice for determining gene function and bacterial, yeast, and mammalian cells. The primary methods used in site-directed gene manipulation rely on gene replacement via homologous recombination using an appropriately designed gene targeting vector. In plants, gene targeting has been limited by the frequency of homologous recombination. Even with improvements in transformation and selection methods, the frequency of gene targeting in plants is still $10^{-3}$–$10^{-4}$ fold lower than random integration.

New procedures are being developed for mammalian gene therapy. One example is an approach using chimeric RNA/DNA oligonucleotides. In mammalian cells, chimeric oligonucleotides that contain both DNA/DNA and RNA/DNA duplex regions with homology to a target locus, are capable of specifically correcting mutations at a high frequency in both episomal and chromosomal target genes. Recently, mutations in liver alkaline phosphatase gene and factor IX gene have also been efficiently corrected in human hepatoma cells. However, to date, chimeric oligonucleotide-based gene targeting has not been reported in plant systems.

Herbicide resistant forms of plants are desirable for many breeding and crop production applications. Approaches to date have involved laborious methods including: finding a naturally existing form of resistance in a plant and introgressing the trait into desirable germplasm; mutagenesis of plants, seeds, and seedlings to generate novel mutant plants that confer resistance and introgressing the trait into the breeding population; finding a naturally existing form of a gene which confers resistance to a target herbicide and introducing the gene into the desired species by transformation; and, converting a wild type gene to a resistant form by mutagenesis. All of these approaches rely on either natural recovery of the trait or modification of the gene and subsequent introduction of the resistance gene into a plant.

A major disadvantage in each of these approaches is the time involved in terms of mutagenesis, recovery of the trait and the breeding necessary to introduce the trait into desired populations. Further, where transformation is involved, plants will have to be tested and selected that are not impacted by expression instability or by poor agronomic performance. Additionally, in many instances, optimum performance of a gene in a given species may only be achieved following resynthesis of the gene to maximize usage of preferred codons, or by the creation of modified forms of the gene.

Because of the present problems associated with the integration and expression of foreign genes in plant cells, effective strategies for modification, conversion or correction of gene sequences are needed.

SUMMARY OF THE INVENTION

Compositions and methods for modifying nucleotide sequences of interest in a plant cell are provided. The compositions comprise single covalently linked duplex oligonucleotides, a portion of which are homologous to a plant nucleotide sequence of interest. The oligonucleotides comprise both deoxyribonucleotides and ribonucleotides. To create a modified plant sequence the oligonucleotides contain within the region of homology to the native plant sequence at least one noncorresponding or heterologous base pair that replaces the naturally occurring sequence in the plant genome.

The chimeric oligonucleotide used for target site conversion consists of a single-stranded nucleic acid designed to form a duplex structure capped by single-stranded loops. One strand of the duplex pairs with the target sequence of the plant. This strand consists of a deoxyribonucleotide stretch of nucleotides with at least one mismatch to the target sequence, flanked by two sequence-specific targeting segments of 2'-O-methyl ribonucleotides. The lower strand of the duplex contains only deoxyribonucleotides. Homologous pairing between the chimeric oligonucleotide and the plant's target sequence and the strand transfer process are enhanced by the modified RNA residues.

The method involves converting or modifying the nucleotide sequence of interest in the plant cell by recombination or repair between homologous sequences, in the duplex oligonucleotide and the plant nucleotide sequence. The process exchanges the heterologous base pairs for the naturally occurring base pairs. Plants having the converted or modified sequence can be obtained. The methods are useful for making a variety of sequence-specific changes for applications such as site-specific mutagenesis, gene knockout, allelic replacement, and the like.

In a particular embodiment, compositions and methods for generating herbicide resistant plants are provided. The compositions comprise single covalently linked duplex oligonucleotides that are homologous with a nucleotide sequence of interest except for base pairs necessary to convert the sequence to a herbicide resistant form of the gene. The method involves converting the naturally occurring nucleotide sequence in a plant by targeted gene conversion to create a herbicide resistance form of the gene. Herbicide resistant plants can be obtained from the method.

BRIEF DESCRIPTION OF THE FIGURES

FIG. 1 provides a chimeric oligonucleotide comprising three intervening blocks of RNA residues for modification of the maize EPSPS gene to a herbicide resistant form of the gene by converting two nucleotides at each of two amino acid residues of the target sequence. The linear and active forms of the oligonucleotide (SEQ ID NO: 1) are provided. A fragment of the maize EPSPS amino acid sequence is translated beneath the active oligonucleotide and is set forth in SEQ ID NO: 22.

FIG. 2 provides a chimeric oligonucleotide comprising three intervening blocks of RNA residues for modification of the maize EPSPS gene to a herbicide resistant form of the gene by converting one nucleotide at each of two amino acid residues of the target sequence. The linear and active forms of the oligonucleotide (SEQ ID NO: 2) are provided. A fragment of the maize EPSPS amino acid sequence is translated beneath the active oligonucleotide and is set forth in SEQ ID NO: 23.

FIG. 3 provides a chimeric oligonucleotide comprising two intervening blocks of RNA residues for modification of the maize EPSPS gene to a herbicide resistant form of the gene by converting two nucleotides at each of two amino acid residues of the target sequence. The linear and active forms of the oligonucleotide (SEQ ID NO: 3) are provided. A fragment of the maize EPSPS amino acid sequence is translated beneath the active oligonucleotide and is set forth in SEQ ID NO: 23.

FIG. 4 provides a chimeric oligonucleotide comprising two intervening blocks of RNA residues for modification of the maize EPSPS gene to a herbicide resistant form of the gene by converting one nucleotide at each of two amino acid residues of the target sequence. The linear and active forms of the oligonucleotide (SEQ ID NO: 4) are provided. A fragment of the maize EPSPS amino acid sequence is translated beneath the active oligonucleotide and is set forth in SEQ ID NO: 23.

FIG. 5 provides a chimeric oligonucleotide comprising two intervening blocks of RNA residues for modification of the maize EPSPS gene to a herbicide resistant form of the gene by converting two nucleotides at each of two amino acid residues of the target sequence. The first amino acid residue target is within a DNA region while the second amino acid residue target is within an RNA region. The linear and active forms of the oligonucleotide (SEQ ID NO: 5) are provided. A fragment of the maize EPSPS amino acid sequence is translated beneath the active oligonucleotide and is set forth in SEQ ID NO: 22.

FIG. 6 provides a chimeric oligonucleotide comprising two intervening blocks of RNA residues for modification of the maize EPSPS gene to a herbicide resistant form of the gene by converting one nucleotide at each of two amino acid residues of the target sequence. The first amino acid residue target is within a DNA region while the second amino acid residue target is within an RNA region. The linear and active forms of the oligonucleotide (SEQ ID NO: 6) are provided. A fragment of the maize EPSPS amino acid sequence is translated beneath the active oligonucleotide and is set forth in SEQ ID NO: 24.

FIG. 7 provides a chimeric oligonucleotide comprising two intervening blocks of RNA residues for modification of the maize EPSPS gene to a herbicide resistant form of the gene by converting two nucleotides at each of two amino acid residues of the target sequence. The first amino acid residue target is within an RNA region while the second amino acid residue target is within a DNA region. The linear and active forms of the acid sequence is translated beneath the active oligonucleotide and is set forth in SEQ ID NO: 22.

FIG. 8 provides a chimeric oligonucleotide comprising two intervening blocks of RNA residues for modification of the maize EPSPS gene to a herbicide resistant form of the gene by converting one nucleotide at each of two amino acid residues of the target sequence. The first amino acid residue target is within an RNA region while the second amino acid residue target is within a DNA region. The linear and active forms of the oligonucleotide (SEQ ID NO: 8) are provided. A fragment of the maize EPSPS amino acid sequence is translated beneath the active oligonucleotide and is set forth in SEQ ID NO: 24.

FIG. 9 provides a chimeric oligonucleotide for a single amino acid modification of the maize EPSPS gene to a herbicide resistant form of the gene. The amino acid target here corresponds to the first of the two amino acid residues targeted by the chimeric oligonucleotides in FIGS. 1–8. The linear and active forms of the oligonucleotide (SEQ ID NO: 9) are provided. A fragment of the maize EPSPS amino acid sequence is translated beneath the active oligonucleotide and is set forth in SEQ ID NO: 25.

FIG. 10 provides a chimeric oligonucleotide for a single amino acid modification of the maize EPSPS gene to a herbicide resistant form of the gene. The amino acid target here corresponds to the second of the two amino acid residues targeted by the chimeric oligonucleotides in FIGS. 1–8. The linear and active forms of the oligonucleotide (SEQ ID NO: 10) are provided. A fragment of the maize EPSPS amino acid sequence is translated beneath the active oligonucleotide and is set forth in SEQ ID NO: 26.

FIG. 11 provides a chimeric oligonucleotide for a single amino acid modification at amino acid position 621 of the maize AHAS gene to a herbicide resistant form of the gene. The linear and active forms of the oligonucleotide (SEQ ID NO: 11) are provided. A fragment of the maize AHAS amino acid sequence is translated beneath the active oligonucleotide and is set forth in SEQ ID NO: 27.

FIG. 12 provides a chimeric oligonucleotide for a single amino acid modification at amino acid position 165 of the maize AHAS gene to a herbicide resistant form of the gene. The linear and active forms of the oligonucleotide (SEQ ID NO: 12) are provided. A fragment of the maize AHAS amino acid sequence is translated beneath the active oligonucleotide and is set forth in SEQ ID NO: 28.

FIG. 13 provides a chimeric oligonucleotide for a single nucleotide modification which converts a stop codon to a codon encoding tyrosine in a transgene target previously introduced into maize (see text). The linear and active forms of the oligonucleotide (SEQ ID NO: 13) are provided. A fragment of an amino acid sequence is translated beneath the active oligonucleotide and is set forth in SEQ ID NO: 29.

DETAILED DESCRIPTION OF THE INVENTION

Compositions and methods for targeted gene correction, conversion, or modification in plants are provided. The method involves the targeted correction, modification, or mutation of nucleotide sequences in a plant cell based on homology between a modifying oligonucleotide and the corresponding target plant DNA sequence. The compositions for use in the method are RNA-DNA hybrid oligonucleotides, referred to herein as chimeric oligonucleotides, that exploit the natural recombinogenecity of RNA-DNA hybrids. The chimeric oligonucleotides contain both DNA/DNA and RNA/DNA duplex regions with homology to the plant target locus or sequence. Such sequences are capable of introducing nucleotide changes at a high frequency in the target sequence.

The chimeric oligonucleotides of the invention are duplex oligonucleotides having a region of homology, the modifying sequence, with a gene or nucleotide sequence of interest in the plant, the target. The chimeric oligonucleotides comprise both deoxyribonucleotides and ribonucleotides. The chimeric oligonucleotides of the invention consist of a single-stranded nucleic acid designed to form a duplex structure that is capped by single-stranded loops. One strand of the duplex is capable of complementary pairing with the target sequence in the plant genome and comprises the modifying sequence, a DNA sequence of several nucleotides with at least one mismatch to the target sequence. This modifying DNA sequence is flanked by two sequence-specific targeting segments of several 2'-O-methyl ribonucleotides. The opposite strand of the duplex comprises deoxyribonucleotides.

The design of the chimeric oligonucleotide, or vector, is based on the discovery that RNA-DNA hybrids are highly active in homologous pairing reactions in vitro. Hairpin caps constructed at the ends of the hybrid molecule present no impediment to pairing, and protect the vector from exonucleolytic degradation. The vector is activated for recombination by the incorporation of RNA residues. Homologous pairing between the chimeric oligonucleotide and the target sequence as well as the strand transfer process are enhanced by the modified RNA residues.

The chimeric oligonucleotides of the invention can be constructed as single nucleic acid polymers. Thus, the chimeric oligonucleotides must contain at least one region, preferably at least two regions, of at least one base, preferably at least about two to about five bases, more preferably at least about three or about four bases that are not Watson-Crick paired. The unpaired bases serve as linkers or hairpin caps between the two strands of Watson-Crick paired bases.

By "duplex" is intended a single nucleic acid polymer which through intramolecular base pairing is capable of folding back on itself to form a double stranded molecule.

By "hybrid-duplex" is intended a Watson-Crick duplex molecule having both DNA and RNA. For example, a DNA molecule and its mRNA can form a hybrid duplex. A duplex molecule comprising two DNA molecules is a homo-duplex.

U.S. Pat. No. 5,565,350 ('350) describes chimeric oligonucleotides which are useful for targeted gene correction and methods for their use in cultured mammalian cells. The terminology used herein is patterned after the 3350 patent. Such disclosure is herein incorporated by reference. The present invention utilizes the methods set forth in the U.S. Pat. No. 5,565,350 patent to correct gene sequences in plants. That is, the present oligonucleotides are designed to modify naturally occurring or native nucleotide sequences in plants by at least one nucleotide.

The chimeric oligonucleotides of the invention are designed as a single molecule, with two sequences that are inverted and complementary, capable of folding back on itself to form a duplex structure. The oligonucleotide comprises DNA residues with at least two intervening blocks of 2'-O-methyl RNA residues flanking a short stretch of DNA residues, a DNA block. The addition of 2'-O-methyl RNA residues provides added protection from RNAse activity. The number of RNA residues may vary. Usually, from about thee to about twenty, preferably about four to about fifteen residues are utilized, more preferably about five to about ten residues. Generally, when the oligonucleotide is folded into the duplex conformation, one nucleotide strand is comprised of all DNA residues whereas the other strand is comprised of RNA-DNA blocks of residues.

The region of DNA flanked by the RNA regions is designed to introduce alterations in the target or complementing nucleotide sequence in the plant cell. Thus, it is recognized that the region of DNA residues which are flanked by the RNA residues may vary depending upon the changes to be incorporated into the native gene. That is, where a single point mutation is being inserted, a short stretch of DNA residues is utilized, generally from about three to about eight, preferably about five. Where multiple residues are being inserted into the plant genome, longer stretches of DNA will be necessary. Likewise, where more than one point mutation is being made, the stretch of DNA will be determined by the location of the specific site changes. Thus, it is recognized that the length of the DNA block or modifying sequence, may vary from about five to more than about 60 nucleotides; preferably from about eight to about 50 nucleotides, more preferably from about 10 to about 30 nucleotides.

It is further recognized that where more than one point mutation is being inserted into the genome, that the chimeric oligonucleotide can be constructed to have more than two flanking RNA sequences. That is, RNA residues may flank more than one modifying DNA sequence. Such a design may provide better stability and recombination efficiency where the sites of mutation or modification are not contiguous.

The oligonucleotide is designed to fold into a duplex conformation, the sequence of one strand comprising all DNA residues with the other strand comprising RNA-DNA blocks. In the same manner, it is recognized that the total length of the chimeric oligonucleotide will vary depending upon the target region in the plant cell. The chimeric oligonucleotides of the invention are intended to specifically introduce alterations into a target gene or nucleotide sequence. The genetic site of the alteration is determined by selecting a portion of the chimeric oligonucleotide to have the same sequence as the sequence of the target. That is, the portion of the chimeric oligonucleotide is homologous with the target site. The chimeric oligonucleotides are designed to have at least two homologous regions flanking an interposed heterologous region. The heterologous region contains the "mutator" base pairs or sequence to be introduced into the target. In this manner, a predetermined alteration can be made in the target sequence.

Methods for construction of the chimeric oligonucleotides of the invention are known in the art. The oligonucleotides can be synthesized by solid phase synthesis. See, Caruthers, M. H. (1985) *Science* 230:281–285; Itakura et al. (1984) *Ann. Rev. Biochem.* 53:523–556. Such methods may be modified to permit the synthesis of RNA and RNA-DNA chimeric molecules. See, for example, Scaringe et al. (1990) *Nucleic Acids Research* 18:5433–5441; Usman et al (1992) *Nucleic Acids Research* 20:6695–6699; Swiderski et al. (1994) *Anal. Biochem.* 216:83–88; Usman and Cedergren (1992) *Trends Biochem. Sci.* 17:334–339; Yoon et al. (1996) *Proc. Natl. Acad. Sci. USA* 93:2071–2076; Cole-Strauss et al. (1996) *Science* 273:1386–1389; and Kren et al. (1997) *Hepatology* 25:1462–1468. Such disclosures are herein incorporated by reference. Generally, chimeric oligonucleotides are constructed having a homo-duplex region interspersed between two hybrid-duplex regions. Two synthetic chimeric polynucleic acids, each having a hairpin conformation are constructed. The two molecules are synthesized with unique staggered free ends that correspond to specific restriction enzyme products. These staggered ends complement those that are constructed at each end of the homo-duplex region. The two chimeric nucleic acids and the homo-duplex region are then ligated together to form the complete hybrid-duplex molecule. General methods for DNA manipulation are known in the art. See, for example, *Molecular Cloning*, Sambrook et al. (eds.) Cold Spring Harbor Laboratory Press (1989).

As indicated, the compositions and methods of the invention are useful for targeted gene correction, site-specific mutagenesis, gene knockout, allelic replacement and genetic modification of plant genomes. Furthermore, the methods can be used to create a predetermined nucleotide pair mismatch in a target sequence of the genome of a plant or plant cell upon which endogenous mismatach repair mechanisms can operate to create a nucleotide alteration at or near the target sequence. The methods are useful for modulating the activity of genes of interest. In one embodiment, herbicide resistant plants are created by modifying existing genes within the plant genome. Such genes include the 5-enol pyruvylshikimate-3-phosphate synthase (EPSPS) gene and the acetohydroxy acid synthase (AHAS or ALS). Alternatively, the methods are useful for inactivating a gene, particularly a gene that has been introduced into the plant genome by transformation methods. Genes of particular interest include herbicide, S marker (scorable and selectable) genes and the like.

In this manner, the chimeric oligonucleotides of the invention can be used to introduce a modification in a specific genomic location in a target plant cell. The specific location of the modification is defined by the nucleic acid sequence called the target sequence. According to the methods of the invention, the chimeric oligonucleotide is constructed wherein the homologous regions are identical to the target sequence, except for the presence of some heterologous nucleotides of the hybrid-duplex. The change to be introduced is encoded by the heterologous region. As indicated above, the change may be in substituting one or more than one bases of the sequence, adding one or more bases, or deleting one or more bases in the native gene.

The constructed chimeric oligonucleotides are introduced into the nucleus of the plant cell by any method available in the art. In this manner, genetically modified plants, plant cells, plant tissue, seed, and the like can be obtained. The chimeric oligonucleotides may be introduced into the plant by one or more techniques typically used for direct DNA delivery into cells. Such protocols may vary depending on the type of plant or plant cell, i.e. monocot or dicot, targeted for gene modification. Suitable methods of transforming plant cells include microinjection (Crossway et al. (1986) *Biotechniques* 4:320–334), electroporation (Riggs et al. (1986) *Proc. Natl. Acad. Sci. USA* 83:5602–5606, direct gene transfer (Paszkowski et al. (1984) *EMBO J.* 3:2717–2722), and ballistic particle acceleration (see, for example, Sanford et al., U.S. Pat. No. 4,945,050; WO 91/10725 and McCabe et al. (1988) *Biotechnology*, 6:923–926). Also see, Weissinger et al. (1988) *Annual Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Biotechnology* 6:923–926 (soybean); Datta et al. (1990) *Biotechnology* 8:736–740 (rice); Klein et al. (1988) *Proc. Natl. Acad. Sci. USA*, 85:4305–4309 (maize); Klein et al. (1988) *Biotechnology*, 6:559–563 (maize); WO 91/10725 (maize); Klein et al. (1988)*Plant Physiol.* 91:440444 (maize); Fromm et al. (1990) *Biotechnology* 8:833–839; and Gordon-Kamm et al. (1990) *Plant Cell* 2:603–618 (maize); Hooydaas-Van Slogteren & Hooykaas (1984) *Nature* (London) 311:763–764; Bytebier et al. (1987) *Proc. Natl. Acad. Sci. USA* 84:5345–5349 (Liliaceae); De Wet et al. (1985) In The *Experimental Manipulation of Ovule Tissues*, ed. G. P. Chapman et al., pp. 197–209. Longman, N.Y. (pollen); Kaeppler et al. (1990) *Plant Cell Reports* 9:415–418; and Kaeppler et al. (1992) *Theor. Appl. Genet.* 84:560–566 (whisker-mediated transformation); U.S. Pat. No. 5,693,512 (sonication); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750; all of which are herein incorporated by reference.

The cells which have been altered by the methods of the invention may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited.

The following examples are offered by way of illustration and not by way of limitation.

EXPERIMENTAL

Example 1

Design of Chimeric Oligonucleotides

N-phosphonomethylglycine, also known by its common name glyphosate is widely used as a herbicide. Herbicide tolerant plants have been constructed by utilizing EPSPS genes which are capable of conferring tolerance to a plant. In these instances, glyphosate resistance genes are recovered and utilized to transform plant cells and regenerated plants obtained which are glyphosate resistant. A glyphosate resistant gene has been published carrying double mutations. See, WO 97/04103, herein incorporated by reference. The publication describes the transformation of tobacco with the mutant form of the gene.

The mutant form of the gene conferring glyphosate resistance can be created utilizing the targeted gene correction method described herein. Two chimeric oligonucleotides are designed as a single molecule with two sequences that are inverted and complementary, capable of folding back on itself to form a duplex structure. One form of the molecule comprises DNA residues with three intervening blocks of 2'-O-methyl RNA residues. The linear and active forms of such oligonucleotides are depicted in FIGS. 1 and 2. See SEQ ID NOs: 1 and 2 for the linear forms.

Chimeric oligonucleotides can also be constructed having two intervening blocks of RNA residues. See FIGS. 3 to 8 for the linear forms (SEQ ID NOs: 3–8) and active oligonucleotide conformations of these molecules.

Alternatively, two chimeric oligonucleotides can be constructed, each singly designed to target creation of one or the other of the two mutations described in FIGS. 1 to 8. See FIGS. 9 and 10 for the linear (SEQ ID NOs: 9–10) oligonucleotide as well as the active oligonucleotide conformations. In this example, the two constructs can be introduced into a plant cell separately or together.

Synthesis and Purification of Oligonucleotides

The chimeric oligonucleotides are synthesized on a 0.2 μmol scale by using the 1000-Å-wide-pore CPG on the ABI 394 DNA/RNA synthesizer. The exocyclic amine groups of DNA phosphoramidites (Applied Biosystems) are protected with benzoyl for adenosine and cytidine and isobutyryl for guanosine. The 2'-O-methyl RNA phosphoramidites (Glen Research, Sterling, Va.) are protected with a phenoxyacetyl group for adenosine, dimethylformamide for guanosine and an isobutyryl group for cytidine. After the synthesis is complete, the base-protecting groups are removed by heating in ethanol/concentrated ammonium hydroxide, 1:3 (vol/vol), for 20 h at 55° C. The crude oligonucleotides are purified by polyacrylamide gel electrophoresis. The entire oligonucleotide sample is mixed with 7 M urea/10% (vol/vol) glycerol, heated to 70° C., and loaded on a 10% polyacrylamide gel containing 7 M urea. After gel electrophoresis, DNA is visualized by UV shadowing, dissected from the gel, crushed, and eluted overnight in TE buffer (10 mM Tris.HCl/1 mM EDTA, pH 7.5) with shaking. The eluent containing gel pieces is centrifuged through 0.45 μm (pore size) spin filter (Millipore) and precipitated with ethanol. Samples are further desalted with a G-25 spin column (Boerhinger Mannheim) and greater than 95% of the purified oligonucleotides are found to be full length.

Chimeric Oligonucleotide Delivery into Plant Cells

A. Delivery of Chimeric RNA-DNA Oligonucleotides into Maize BMS Cells by Projectile Bombardment Day 1

Preparation of Cells:

1. Set up a plastic funnel with Miracloth on a 500 ml side arm flask and connect to a vacuum.
2. Transfer growing BMS cells from one flask to the funnel.
3. Apply vacuum to remove the liquid medium and dry cells as thoroughly as possible.
4. Disconnect the top of the funnel. Weigh and transfer about 2.5 g of cells into tubes.
5. Add 10 ml of 589 medium into each tube, mix cells by pipetting, bring total volume to 50 ml with 589 [Dilute cells 1:20 (w/v) with liquid medium].
6. Set up a glass funnel with filter discs on a side arm flask connected to a vacuum.
7. Apply 5 ml aliquots to each filter disc, turn on the vacuum to dry cells. Turn off the vacuum and transfer cells with the filter disc to 115 solid medium. Culture in the dark.

Day 2—Chimeric Oligonucleotide Delivery by Particle Bombardment

1. Dry cells with glass filter and vacuum. Transfer the cell disc from the medium to a filter-filled petri dish to dry the cells. Label cells for the experiments.
2. Sterilize the microcarrier with 95% ethanol and air dry the edge of a large petri dish. Set the microcarrier into the sterilized carrier holder. Soak the 650 psi rapture discs in 100% isopropanol.
3. Label and dilute oligonucleotides to 1 μg/μl in 0.5 ml sterilized centrifuge tube. Mix 2.5 μl of 1 μg/μl oligonucleotides with 7.5 μl of RNAse-free water.
4. Set sonicator at 8–9, sonicate the gold particles briefly. Distribute 2.5 μl gold particles into each 1.5 ml sterilized centrifuge tube immediately after sonication. Spin down the particles, discard the supernatants.
5. Distribute 10 μl oligonucleotides per tube. Mix with particles by sonication. Add 16.5 μl of 2.5 μM $CaCl_2$ and 6.6 μl of 0.1M spermidine and gently shake for 5–10 min. Centrifuge the mixture for 10 seconds at 10,000 rpm. Discard the supernatant. Sterilize the oligonucleotides and particles by adding 125 μl of 100% ethanol, sonicate and centrifuge briefly, discard the supernatant.
6. Dilute the oligonucleotide/particle mixture to 60 μl with ethanol. Distribute 10 μl onto each macrocarrier (6 shots).
7. Set helium gauge to 900 psi. Turn vacuum pump on (switch, valve, knob).
8. Sterilize the environment. Turn particle gun power on, set screen, microcarrier, rupture discs, and cells. Let vacuum reach 28 mm Hg, hold, fire the gun, release vacuum.
9. Transfer cells back to culture medium, and culture in the dark.

Day 4—Initiate Selection

B. Delivery of Chimeric RNA-DNA Oligonucleotides into Maize Hill Cells by Projectile Bombardment:

Day 1

Preparation of Cells:

1. Set up a plastic funnel with Miracloth on a 500 ml side arm flask with parafilm seals and connect to a vacuum.
2. Add 80–100 ml of 559 liquid medium to the funnel until it reaches to the bottom of the mesh.
3. Transfer the Hill callus from plates to the funnel, and break the callus by pushing through the mesh with the plunger of a 60 ml syringe.
4. Apply vacuum to the liquid medium and dry cells as thoroughly as possible.
5. Disconnect the top of the funnel. Weigh and transfer 2.5 g cells into tubes.
6. Add 10 ml of 559 medium to each tube, mix cells by pipetting, bring total volume to 50 ml with 559 [Dilute cells 1:20 (w/v) with liquid medium].
7. Set up a glass funnel with filter discs on a side arm flask connected to vacuum.
8. Apply 5 ml aliquots to each filter disc, turn on the vacuum to dry cells. Turn off the vacuum and transfer cells with filter disc to 608 solid medium (560P without, 2,4-D). Culture in the dark.

Day 2

Chimeric Oligonucleotide Delivery by Particle Bombardment:

1. Dry cells with glass filter and vacuum. Transfer the cell disc from the 608 medium to a filter-filled petri dish to dry the cells.
2. Sterilize the microcarrier with 95% ethanol and air dry the edge of a large petri dish. Set the microcarrier into the sterilized carrier holder. Soak the 650 psi rapture discs in 100% isopropanol.
3. Label and dilute oligonucleotides to 1 μg/μl in 0.5 ml sterilized centrifuge tube. Mix 2.5 μl of 1 μg/μl oligonucleotides with 7.5 μl of RNAse-free water.
4. Set sonicater at 8–9, sonicate the gold particles briefly. Distribute 25 μl old particles into each 1.5 ml sterilized centrifuge tube immediately after sonication. Spin down the particles, discard the supernatants.

5. Distribute 10 $\mu$l oligonucleotides per tube. Mix with particles by sonication. Add 16.5 $\mu$l of 2.5 $\mu$M $CaCl_2$ and 6.6 $\mu$l of 0.1M spermidine and gently shake for 5–10 min. Centrifuge the mixture for 10 seconds at 10,000 rpm. Discard the supernatant. Sterilize the oligonucleotides and particles by adding 125 $\mu$l of 100% ethanol, sonicate and centrifuge briefly, discard the supernatant.
6. Dilute the oligonucleotide/particle mixture to 60 $\mu$l with ethanol. Distribute 10 $\mu$l onto each microcarrier.
7. Set helium gauge to 900 psi. Apply vacuum.
8. Turn vacuum on, let reach 28 mm Hg, hold, fire gun, release vacuum.
9. Transfer cells back to culture medium, and culture in the dark.

Day4

Initiate Selection

C. Selection for Chemical Resistance Conferred by Introducing a Mutation in a Maize EPSPS Gene Selection of Glyphosate-Resistant Hill Cells:

1. Two days after bombardment, transfer the cell from growth medium plates to 2.5 mM glyphosate media, and culture in the dark.
2. Six days after bombardment, prepare 50 ml centrifuge tubes, add 5 ml melted medium to each.
3. Transfer cells from the filter discs to the tubes when the agar cools down. Mix cells by repeatedly pipetting.
4. Distribute 2.5 ml cell mixture to each plate containing 2.5 mM glyphosate. Uniformly plate cells. Culture in the dark.
5. Select the growing cells.

Selection of glyphosate-Resistant BMS Cells:

1. Two days after bombardment, prepare 50 ml centrifuge tubes, add 4–5 ml liquid medium containing glyphosate.
2. Transfer cells from the filter discs to the tubes. Mix cells by repeatedly pipetting with a wide-mouth 10 ml glass pipet.
3. Distribute 1 ml cell mixture to each plate containing glyphosate medium.
4. Select the growing cells.

Example 2

Materials and Methods

Transformation vectors—The plasmid pPHPP10247 contains the in vitro mutagenized maize AHAS gene encoding the Ser621Asn mutant form of AHAS. This gene is under the control of the 2.0 kb maize Ubiquitin-1 promoter (bases −899 to +1093, Christensen et al. (1992) *Plant Mol. Biol.* 18:675–689) and a 280 bp fragment containing the nopaline synthase polyadenylation signal (Bevan et al. (1983) *Nucl. Acids Res.* 11:369–385). The plasmid pPHP12322 contains the maize Ubiquitin-1 promoter driven, in vitro mutagenized maize AHAS gene which encodes the Pro165A1a mutant form of AHAS. The plasmid used to confer resistance to the herbicide bialaphos, pPHP3528, consists of an enhanced CaMV35S promoter (bases −421 to −90 and −421 to +2, Gardner et al. (1981) *Nucl. Acids Res.* 9:2871–2888), a 79 bp fragment from the 5' leader sequence of tobacco mosaic virus (Gallie et al. (1987) *Nucl. Acids Res.* 15:3257–3273), the first intron of the maize ADH1-S gene (Dennis et al. (1984) *Nucl. Acids Res.* 12:3983–3990), the coding sequence of the *Streptomyces hygroscopicus* bar gene (Thompson et al. (1987) *EMBO J.* 6:2519–2523), and the potato proteinase II (pinII) terminator (bases 2 to 310, An et al. (1989) *Plant Cell* 1:115–122). Both pPHP10247 and pPHP3528 have pUC derived backbones.

For the transgene target a translational fusion between phosphinothricin-N-acetyltransferase, pat (Wohlleben et al. (1988) *Gene* 70:25–37) and the green fluorescence protein, GFP (Prasher et al. (1992) *Gene* 111:229–233) was created pat is a functional analog of the bar gene that similarly detoxifies Bialaphos. The coding sequences of GFP and pat have been modified to utilize maize preferred codons to enhance expression, these modified genes are referred to as GFPm and mo-PAT respectively. See, for example, U.S. application Ser. No. 09/003,287. A fusion was initially created by cloning the 3' BglII site in mo-PAT to a 5' flanking BamHI site on GFPm. Site directed mutagenesis (MORPH kit, 5'-3' Boulder, Colo.) was then used to remove the start codon (ATG) from GFPm to ensure low background expression of GFPm in target lines. Using the oligonucleotide PHN14593, 5'CGGTGACGCAGATCTATCCAACATTGTCCAAGGG C3'(SEQ ID NO: 14) the BglII site was recreated in mo-PAT and the start codon of GFPm was removed simultaneously. Four amino acids, YPTS, form the junction in the mo-PAT/GFPm sequence. The vector pPHP 10699, is a positive control mo-PAT/GFPm fusion cloned under the control of the maize Ubiquitin-1 promoter and pinII terminator in a pUC-derived plasmid backbone.

To create the target sequence for correction, the native pat stop codon (TGA) was inserted in the junction of mo-PAT/GFPm. Site-directed mutagenesis of pPHP10699 with oligonucleotide PHN16214, 5'GGTGACGCAGATCTAGGTACCATCGTCCAAGGGC GAG3', (SEQ ID NO: 15) was used to change the junction sequence from YPTS to *VPS and to introduce a KpnI site adjacent to the stop codon. This creates a sequence that only expresses mo-PAT, but with correction to remove the stop codon, GFPm expression results. When making corrections to this target, changing the TAG stop codon to TAC also knocks out the KpnI site and creates a novel SnaBI site. The vector pPHP11207, contains the mo-PAT/TAG/GFPm target sequence, cloned with the maize Ubiquitin-1 promoter and pinII terminator, and inserted into a superbinary vector pSB 1 for Agrobacterium mediated transformation of maize (Ishida et al. (1996) *Nature Biotech.* 14:745–750).

Cell Culture, transformation, and selection—Friable embryogenic calli (type II) were initiated from immature embryos of the "HiII" maize germplasm (Armstrong et al. (1991) *Maize Genet. Coop. Newslett.* 65:92–93), and maintained on N6 basal media with 3% (w/v sucrose, 2 mg/l 2,4-dichlorophenoxyacetic acid (2,4-D), 0.7 mg/l L-proline, 0.85 mg/l $AgNO_3$, and 0.3% (w/v) GELRITE® (Sigma, St. Louis). Nonregenerable maize Black Mexican sweet (BMS-S4) suspension cultures were maintained in a liquid MS medium containing 2 mg/l 2,4-D. The cultures were incubated at 26° C. on a shaker in the dark. Cells were harvested and transformed according to Kirihara (1994).

The transgenic AHAS mutants were established by co-transformation of one of the plasmids pPHP10247 (AHAS621) or pPHP12322 (AHAS 165) and pPHP3528 using particle bombardment-mediated transformation according to the procedures of Tomes et al. (1995) *Plant Cell Tissue and Organ Culture: Fundamental Methods*; Gamborg O L, Philips G C (eds.) pp. 197–213. Springer-Verlag, Berlin, Heidelberg. Plasmid particle loading and delivery were done with a helium-powered particle acceleration device, PDS 1000 (Bio-Rad, Hercules, Calif.). Transformants expressing the bar gene were selected on media containing 3 mg/l bialaphos (Meiji Seika, Yokohama, Japan), according to Register et al. (1994) *Plant Mol. Biol.* 25:951–961, and further selected on imazethapyr or chlorsulfuron (see below).

Stable Hill cell lines with a maize codon usage optimized moPAT/GFPm transgene were established via Agrobacterium-mediated transformation (Ishida et al. (1996) *Nature Biotech.* 14:745–750). Transformed immature embryos were selected on media containing 3 mg/l bialaphos.

Selection of AHAS mutants was conducted according to Anderson and Georgeson (1989) *Genome* 31:994–999 with modification. Following microprojectile bombardment with chimeric oligonucleotides, cells were resuspended in liquid medium and uniformly plated on solid culture medium containing either 0.7 μM imazethapyr for AHAS621, (AC263,499, or Pursuit(®, technical grade, American Cyanamid, Princeton, N.J.) or 20 ppb chlorsulfuron for AHAS 165 (Glean®, technical grade, DuPont, Wilmington, Del.). Cells were cultured in the dark room at 25° C., 75% relative humidity for 4–6 weeks. Putative events were subsequently selected in fresh media containing 1.0–2.0 μM imazethapyr or 50 ppb chlorsulfuron.

Plants were regenerated from Hill embryogenic callus containing verified converted PAT/GFP according to (Armstrong et al. (1991) *Maize Genet. Coop. Newslett.* 65:92–93, Register et al. (1994) *Plant Mol. Biol.* 25:951–961). Developing T0 plantlets were transferred to soil and grown to maturity in the greenhouse. Seeds of T1 were collected and germinated for the segregation analysis.

Oligonucleotide synthesis, purification, labeling and plant nuclease-resistance —Chimeric RNA/DNA oligonucleotides PHPC917A, PHPC165A, and PHPC621A were synthesized and purified according to Yoon et al. (1996) *Proc. Natl. Acad. Sci. USA* 93:2071–2076 and Cole-Strauss et al. (1997) *Antisense Nucl. Acid Drug Dev.* 7:211–216. The crude oligonucleotides were purified by PAGE and analyzed by HPLC. DNA and 2'-O-methyl RNA oligonucleotides were synthesized in a similar fashion using either DNA or 2'-O-methyl RNA phosphoramidites. Hybrid molecules of DNA and 2'-O-methyl RNA were prepared by denaturing and re-annealing. Chimeric oligonucleotide SC2 (Cole-Strauss et al. (1996) *Science* 273:1386–1389) was 3'-end labeled with tetramethylrhodamine-6-dUTP (Boehringer Mannheim, Indianapolis, Ind.) using terminal transferase according to the manufacturer's instructions.

Nuclease digestion of oligonucleotides—Whole cell extract (WCE) was prepared from maize BMS cells using a Bionebulizer (Glas-Col, Terre Haute, Ind.) according to Mahajan and Zuo (submitted). Double-strand DNA, 2'-O-methyl-RNA, DNA/RNA hybrid, and RNA/DNA chimera, with similar length and secondary structure, were labeled with $^{32}$p using T4 polynucleotide kinase, and diluted to approximately 50,000 cpm/μl. Samples with the same amount of radioactivity were incubated with WCE at 17° C. for 90 minutes. Controls included incubation in sterilized water and WCE inactivated at 65° C. for 5–10 minutes. Results were examined by 12% polyacrylamide gel electrophoresis (PAGE) and autoradiography. The percentages of intact oligonucleotide in each sample were quantified from the autoradiogram using AlphaEase software (Alpha Innotech, San Leandro, Calif.).

Delivery of chimeric oligonucleotides—Cultured maize cells were suspended in liquid N6 media and then plated on a glass fiber filter (VWR, Westchester, Pa.). Chimeric oligonucleotides were delivered into the maize cells via biolistic bombardment. Oligonucleotides (0.4 μg) were co-precipitated with 15 μl of 2.5, M $CaCl_2$ and 5 μl of 0.1 M spermidine onto 25 μg of 1.0 μm gold particles (Analytical Scientific Instruments, Richmond, Calif.). Microprojectile bombardment was performed using a PDS-1000 He particle delivery system (BioRad, Hercules, Calif.) with 650 psi bombardment pressure, 9 cm target distance and osmotic pretreatment.

Fluorescent microscopy—The in vivo fate of the rhodamine-labeled chimeric oligonucleotides was monitored using a Leica DM RB microscope (Wetzlar, Germany) with filter #41002b (Chroma Technology, VT). Images were recorded by a CH350 CCD camera (Photometrix Inc., Tucson, Ariz.). Superimposed images were processed using Adope Photoshop 4.0. Green fluorescence from GFP expressing cells were surveyed using a Leica MD- 10 epifluorescene microscope with a Leica GFP filter set (10446093) four days after transformation. Images were recorded on the Fujichrome Sensia (ASA400).

PCR amplification and sequence analysis—Target sequences were amplified from the extracted genomic DNA of putative events, by Pwo or Taq polymerase (Boehringer Mannheim, Indianapolis, Ind.) with 30 cycles of 35 seconds at 95° C., 35 seconds at 60° C., and 35 seconds at 72° C. using a MJ thermocycler (MJ Research, Watertown, Mass). For the AHAS621 target, primers common to both AHAS108 and AHAS 109 were designed with the following sequences: 5'GCAGTGGGACAGGTTCTAT (PHN21971) (SEQ ID NO: 16) and 5'AGTCCTGCCATCACCATCCA (PHN21972). (SEQ ID NO: 17) For the AHAS165 target, the following primers were used: 5'ACCCGCTCCCCCGT-CAT (PHN21973) (SEQ ID NO: 18) and 5'ATCTGCT-GCTGGATGTCCTTGG (PHN21974) (SEQ ID NO: 19). For the moPAT/GFPm target, primers used were: 5° C. GCAACGCCTACGACTGGA (PHN21976) (SEQ ID NO: 20) and 5'TGATGCCGTTCTTCTGCTTGTC (PHN21978) (SEQ ID NO: 21). PCR fragments were purified and either cloned (see below) or directly sequenced in both directions on an ABI 377 automated sequencer.

RFLP analysis and cloning—PCR fragments were digested with excess BfaI (New England BioLabs, Beverly, Mass.), and analyzed by electrophoresis on gels containing 2% Metaphor and 1.5% LE agarose (FMS, Rockland, Me.) using 1X Tris-borate EDTA. Undigested bands with mutant alleles were extracted and purified from gel slices using a QIAquick gel extraction kit (Qiagen, Valencia, Calif.) and subcloned into the cloning vectors pCR2.1®-TOPO or pCR-Blunt® (Invitrogen, San Diego, Calif.). Vectors containing subcloned fragment were transformed into competent *E. coli* One-Shot™ Top10 cells (Invitrogen, San Diego, Calif.). Cloned fragments were sequenced using M13 forward and reverse primers.

Results

Introduction of Chimeric Oligonucleotides into Maize Cells

Resistance of chimeric oligonucleotides to maize nucleases—In order to evaluate the stability of chimeric oligonucleotides in plant cells, a preliminary in vitro assay was conducted. Radioactively labeled dsDNA, ds2'-O-methyl-RNA, DNA-2'-O-methyl-RNA hybrid, and DNA-2'-O-methyl-RNA chimeric oligonucleotides with similar length and secondary structure to PHPC917A were incubated with whole cell extract (WCE) from maize. Quantitative analysis indicated each type of oligonucleotide was degraded to about the same extent in maize WCE, with approximately 40–50% remaining undegraded after 90 minutes of incubation.

Delivery of chimeric oligonucleotides and accumulation in maize nuclei—Microprojectile bombardment was used to introduce chimeric oligonucleotides into maize cells. To monitor their in vivo fate, rhodamine-labeled chimeric oligonucleotide SC2 (Cole-Strauss et al. (1996) *Science* 273:1386–1389) was bombarded into onion epidermis and BMS maize suspension culture cells. After bombardment, cells were rinsed with liquid culture media, and examined by fluorescent microscopy at 30 minutes, 1 hour, 2 hours, and 24 hours after bombardment. Other than a diffuse signal in the cytoplasm, rhodamine fluorescence was mainly localized in nuclei, and occasionally associated with gold particles within cells. These data indicate that chimeric oligonucleotides accumulate preferentially in the nuclei of these plant cells. At 24 hours after bombardment, the rhodamine fluorescence was either very weak or no longer visible.

Conversion of Maize Endogenous AHAS

Strategy used for conversion of maize AHAS—According to previous studies, a dominant single point mutation from G to A at nucleotide 1958 of the AHAS coding sequence will lead to resistance to the herbicide imidazolinone in Arabidopsis. This mutation results in an amino acid substitution from Ser (AGT) to Asn (AAT) at the carboxy terminal of the mature AHAS. (Sathasivan et al. (1991) *Plant physiol.* 97:1044–1050, Ott et al. (1996) *J.Mol. Biol.* 263:359–368). The corresponding region (DNA sequences flanking the Ser621 position) was identified in maize and selected for use in the conversion experiments. In maize, there are two copies of AHAS108 and five copies of AHAS109 genes which are identical in nucleotide sequence at the target set (Fang et al. (1992) *Plant Mol. Biol.* 18:1185–1187, Zhu et al. unpublished data). Chimeric oligonucleotide PHPCA621 matches the sequence surrounding Ser621 of both loci, and was designed to modify Ser621 to Asn, while simultaneously removing a BfaI site (FIG. 11 and SEQ ID NO: 11).

Another target selected for this study is maize AHAS Pro 165 which corresponds to ALS Pro196 in tobacco (Lee et al. (1988)). The dominant mutation Pro165A1a caused by a single nucleotide substitution from a CCG to a GCG leads to sulfonylurea herbicide resistance in many species (Lee et al. (1988), Bedbrook et al. (1991), U.S. Pat. No. 5,013,659). Chimeric oligonucleotide PHPCA165 (FIG. 12 and SEQ ID NO: 12) was designed to introduce this mutation into both AHAS108 and AHAS109, since two sequences at this target site are identical. However, no alteration of restriction site was associated with this change.

Recovery of herbicide-resistance events—PHPCA621 and PHPCA165 were introduced into maize cells by microprojectile bombardment respectively. Four to six weeks after initial selection, resistant calli were identified and further sub-cultured on media containing 1–2 μM imazethapyr or 50 ppb chlorsuilfron for at least three months. A number of putative events selected for resistance to 1 μM imazethapyr or 50 ppb chlorsulfuron are summarized in Table 1. These putative events showed the same degree of resistance as the positive mutant control calli, which were created independently by transformation with a vector expressing an engineered Ser621Asn or Pro165A1a mutant form of maize AHAS driven by the maize Ubiquitin-1 promoter. In various negative controls (see below), five spontaneous mutants resistant to imazethapyr were identified from 86 plates (each plate contains approximately $10^6$ cells), and one spontaneous mutant resistant to chlorsulfliron was selected from 50 plates; thus the frequency of spontaneous mutation conferring imazethapyr or chlorsulfuron resistance was determined to be $10^{-7}$–$10^{-8}$.

TABLE 1

Summary of gene conversion experiments

| Target | Cell type | Plates bombarded | Total cells receiving oligos[a] | Putative events selected | Events analyzed[b] | Confirmed mutation | Predicted conversion frequency[d] |
|---|---|---|---|---|---|---|---|
| AHAS621 | HiII | 130 | $2 \times 10^5$ | 40 | 18 | 13 | $1.4 \times 10^{-4}$ |
| AHAS165 | BMS | 86 | $9 \times 10^4$ | 29 | 11 | 9 | $1.0 \times 10^{-4}$ |
| PAT/GFP (T0) | HiII | 48 | $5 \times 10^4$ | 11 | 1 | 1 | $1.5 \times 10^{-4}$ |
| PAT/GFP (T1) | HiII | 89 | $9 \times 10^4$ | 139 | N/D | N/D | $1.1 \times 10^{-3}$ |

[a]Total cells receiving chimeric oligonucleotides were estimated by transient expression of GFP using bombardment of pPHP10699 (16).
[b]Events were selected by their herbicide resistance or GFP phenotypes, and analyzed by direct sequencing of PCR products or, where applicable, by RFLP and cloning.
[c]Mutations induced by chimeric oligonucleotides include those with the desired base change at the target site, as well as base changes at positions adjacent to the target sites (see Table 2).
[d]Predicted conversion frequency = (putative events selected x molecular confirmation rate)/total cells receiving chimeric oligonucleotides In vivo site-directed mutations responsible for herbicide-resistant events—Fragments containing the targeted region of AHAS from herbicide resistant calli were amplified by PCR for sequence analysis. For AHAS621, mutant alleles were first identified by RFLP using BfaI. Fragments containing the wild-type allele produced restriction fragments of 244 bp and 44 bp following digestion, while fragments with the mutant allele remained unrestricted by BfaI. In the positive control where multiple copies of mutant AHAS were introduced by bombardment (data not shown), there are approximately equal amounts of restricted and unrestricted fragments, indicating multiple copies of endogenous wild-type AHAS. Among the fragments amplified from herbicide resistant calli, the restricted fragments are still dominant, suggesting a limited conversion at the target site. However, a band corresponding to unrestricted fragment was clearly present. The unrestricted fragments were isolated and cloned. Sequence analysis indicated that more than 80% of the clones contain the expected change (G to A). Unexpectedly, additional alterations in the adjacent bases were also detected in some sequenced fragments, although at a low frequency. Three alternative mutations observed are shown in Table 2 along with the specific predicted Ser→Asn conversions which predominated. Each of these mutated sequences also resulted in loss of the BfaI restriction site.

TABLE 2

Summary of mutations induced by chimeric oligonucleotides

| | Predicted change | | Observed change | | Frequency of sequence observed | |
|---|---|---|---|---|---|---|
| Target | Nucleotide | Amino Acid | Nucleotide | Amino Acid | Clones[a] | PCR fragments |
| AHAS621 | AGT→AAT | Ser621Asn | AGT→AAT | Ser621Asn | 34/40 | 13/16 |
| | | | AGT→GGT | Ser621Gly | 3/40[b] | 0/16 |
| | | | CCT→CCC | Pro620Pro | 2/40[b] | 0/16 |
| | | | CCT+CAT | Pro620His | 1/40[b] | 0/16 |
| AHAS165 | CCG→GCG | Pro165Ala | CCG→GCG | Pro165Ala | — | 2/12 |
| | | | CCG→TCG | Pro165Ser | — | 7/12 |
| | | | CCG→ACG | Pro165Thr | — | 1/12 |
| PAT/GFP | TAG→TAC | Ter996Tyr | TAG→TAT | Ter996Tyr | — | 1/1 |

[a]Clones were analyzed from 2 independent events.
[b]Frequency enriched by BfaI restriction enzyme digestion.

Sequence alterations from additional calli were examined by direct sequencing of fragments amplified by PCR. Mutated target sequences were observed in fragments amplified from 11 out of 16 imazethapyr resistant calli and two positive control calli, but not in wild-type calli. Thus, 69% of herbicide resistant cells exhibited mutations at or near the target site that could be attributed to chimeric oligonucleotide-mediated gene conversion.

For AHAS 165, targeted PCR fragments from resistant calli and transgenic positive control were sequenced directly. In the transgenic control, the predicted change was detected from the chromatograms. In samples of three chlorsulfuron-resistant calli analyzed, a single nucleotide substitution at the predicted position was also revealed. However, a T rather than an expected G was introduced which resulted in a Pro→Ser conversion (Table 2). Since a substitution for Prol 65 with any amino acid will confer chlorsulfuron resistance (Bedbrook et al. (1991) U.S. Pat. No. 5,013,659), the mutation induced by the chimeric oligonucleotide PHPCA165 resulted in the same expected phenotype.

No mutations at the target position in various negative controls, and no other mutations within the 800 bp surrounding region were found in any of the clones derived from the manipulated cells. The negative controls included: (1) unbombarded cells; (2) cells bombarded with gold particles only; (3) cells bombarded with non-specific PHPC917A chimeric oligonucleotide; (4) cells bombarded with a DNA version of PHPCA621; and (5) herbicide resistant calli arising by spontaneous mutations.

Conversion of a PAT/GFP Transgene

PAT/GFP transgene conversion strategy—The plasmid PHP11129 contains a coding sequence for GFP fused in frame to the PAT gene which encodes phosphinothricin-N-acetyltransferase and confers resistance to bialaphos. Because of an introduced termination codon (TAG) at the end of the PAT coding sequence (position 2987–2990), GFP production is prevented. A chimeric oligonucleotide (PHPC917A) was designed to substitute G with C at nucleotide position 2990 (FIG. 13 and SEQ ID NO: 13). If mismatch repair occurs, the termination codon TAG will be replaced by TAC which will allow expression of the PAT/GFP fusion protein.

Function restoration of silenced GFP by chimeric oligonucleotide PHPC917A—Two Hill transformants containing PHP 11129 were established by selection on bialaphos following Agrobacterium-mediated transformation. No GFP expressing cells were observed in either cell line (data not shown). Four days after introducing chimeric oligonucleotide PHPC917A, GFP expressing cells were identified in each cell line by fluorescence microscopy. In initial experiments using these cell lines maintained for several months in culture, 11 GFP positive events were detected in 48 bombardments. Subsequent experiments utilized freshly initiated cell lines derived from T1 embryos of plants regenerated from the initial transformants; with introduction of chimeric oligonucleotide PHPC917A, the frequency of GFP positive cells was approximately 10-fold higher (Table 1). No GFP positive cells were observed from various negative controls including: (1) unbombarded cells; (2) cells bombarded with gold particles only; (3) cells bombarded with a DNA version of PHPC917A; (4) cells bombarded with non-specific chimeric oligonucleotide PHPCA621; and (5) wild-type cells bombarded with PHPC917A.

GFP positive cell clusters were rescued and transferred to appropriate media for plant regeneration. In regenerated seedlings, GFP expression was clearly seen in the germinating embryo, vascular tissue and epidermal hairs of leaves, and in roots. GFP expression in leaf tissue was partially masked by chlorophyll autofluorescence. Sequence analysis of one of the mutant events indicated replacement of the termination codon by a tyrosine codon. However, a T rather than a predicted C residue was found at the correct nucleotide position 2990. Strong green fluorescence was observed from various tissues of T1 seedlings, except leaves where GFP fluorescence was masked by chlorophyll autofluorescence (data not shown). Segregation analysis of 40 T1 germinating seeds revealed 18 of the seedlings with GFP expression, indicating the 1:1 Mendelian transmission of modified PAT/GEP transgene.

Discussion

In this study, it was demonstrated that genes in maize can be modified at the nucleotide level with a high degree of precision, by using chimeric RNA/DNA oligonucleotides. The manipulated genes could be inherited and stabilized through both mitosis and meiosis, evidenced by the Mendelian inheritance pattern of the PAT/GFP conversion. In the example of the AHAS621 conversion we report here, over 80% of the modifications produced were detected at the expected target nucleotide. The remaining 20% were mutated either at the correct target site but with different nucleotides, or at sites upstream but immediately adjacent to the target nucleotide. In the other two targets (AHAS165 and PAT/GFP) expected phenotypes were recovered, and modifications occurred in a site-directed fashion. However, in both cases, most mutations were due to the substitution of different nucleotides (Table 2). Sequence analysis of up to 800 bp flanking each target site revealed no additional distal modifications. In addition, as reported in previous studies using chimeric RNA/DNA oligonucleotides in mammalian cells (Yoon et al. (1996) *Proc. Natl. Acad Sci. USA* 93:2071–2076), Cole-Strauss et al. (1996) *Antisense Nucl. Acid Drug Dev.* 7:211–216, Xiang et al. (1997) *J. Mol. Med.* 75:829–835, Kren et al. (1997) Hepatology 25:1462–1468 and (1998) *Nature Med.* 4:285–290), no targeted modifications were observed in cells bombarded with either non-target sequence-specific chimeric oligonucleotides or DNA versions of the target sequence-specific oligonucleotides. Chimeric oligonucleotides with sequences identical to the target were not tested in this study. However, previous work in mammalian cells has shown that such oligonucleotides apparently are not mutagenic (Yoon et al. (1996) *Proc. Natl. Acad. Sci. USA* 93:2071–2076 and Cole-Strauss et al. (1996) *Science* 273:1386–1389). The sequence-specific of the modifications reported in this study may be due to the high affinity between the RNA in the chimeric oligonucleotides and the target DNA sequence during homologous pairing (Kotani et al. (1996) *Mol. Gen. Genet.* 250:626–634). Presumably, an endogenous pairing enzyme is also involved (Kmiec et al. (1994) *Mol. Cell. Biol.* 14:7163–7172).

Although different mutated sequences were recovered in several instances from individual herbicide resistant calli, it is not clear from our analysis whether any of the unexpected sequence changes result in the observed herbicide resistance. Similarly, it is not clear which AHAS genes were mutated or if all cells in each callus contained each of the mutated AHAS forms detected by our analysis. At least three possible reasons may contribute to the diversity of modifications at each target site observed in this study. First is the pre-existence of allelic differences among AHAS gene family members. However sequence analysis of over 40 cloned PCR fragments derived from wild-type maize AHAS gene revealed no polymorphism, and two classes of AHAS gene family members (AHAS108 and AHAS109) share the same sequence in the target region (Fang et al. (1992) *Plant Mol. Biol.* 18:1185–1187). Second, it is possible that incorrect chimeric oligonucleotide sequences produced during synthesis were responsible for the unexpected modifications. Although the possibility of misincorporated nucleotides in a small proportion of the chimeric oligonucleotide preparations cannot be completely ruled out, mass spectrometry, HPLC, and independent sequence analysis indicated that the purity of our chimeric oligonucleotide preparation is extremely high (data not shown). Finally, the diversity of mutations may result from decreased fidelity of the mismatch repair machinery in maize, as compared to mammalian cells. Error-prone mismatch repair may somehow be activated by specific sequences in the target region, or by the affinity of the repair machinery for mismatched heteroduplex involving DNA and 2'-O-methyl RNA. Similar unexpected modifications have also been observed occasionally in one or two positions 5' of the target nucleotide in other systems (Ramesh Kumar, personal communication).

The frequencies of site-specific targeting by chimeric oligonucleotides are at least 100-fold higher than spontaneous mutation frequencies. The average of observed gene modification frequencies in our experiments was estimated as 0.2 per bombardment (0.3 putative events per bombardment×0.69 positive molecular confirmations). The number of cells receiving chimeric oligonucleotides, as estimated by transient expression of a GFP marker gene, was $2–4\times10^3$ per bombardment (data not shown). Thus, the frequency of site-directed targeting by chimeric oligonucleotides in maize is approximately $10^{-4}$.

The frequency of site-specific targeting by RNA/DNA oligonucleotides is also significantly higher than gene targeting by homologous recombination. The ratio of targeting by chimeric oligonucleotides to random insertion events is estimated as $4\times10^{-2}$, while the ratio of homologous recombination events to random insertion events is $10^{-5}10^{-4}$ in plants (Paszkowski et al. (1988) *EMBO J.* 7:4021–4026; Lee et al. (1990) *Plant Cell* 2:415–425; Ohl et al. (1994) *Homologous Recombination and Gene Silencing in Plants*; Paszkowski J. (eds.) pp. 191–217; Kluwer Academic Publishers, Dordrecht, The Netherlands; Schaefer and Zrijd (1997) *Plant J.* 11:1195–1206; Thykjaer et al. (1997) *Plant Mol. Biol.* 35:523–530; Kempin et al. (1997) Nature 389:802–803).

The potential use of this system for gene manipulation in genetic and molecular studies, especially for crop improvement, is demonstrated by the ability to achieve proliferation of targeted cells and regeneration of plants. The converted genes were shown to be heritable through both mitosis and meiosis. This contrasts with previous applications of chimeric oligonucleotides in gene therapy, where altered genes were generally not transmitted through mitosis, because the cells targeted, such as lymphoblasts and hepatoma cells, were terminally differentiated (Cole-Strauss et al. (1996) *Science* 273:1386–1389, Kren et al. (1998) *Nature Med.* 4:285–290).

It is recognized that the targeting frequency in maize is three orders of magnitude lower than the frequencies reported for mammalian cells (Cole-Strauss et al. (1996) *Science* 273:1386–1389, Xiang et al. (1997) *J. Mol. Med* 75:829–835, Kren et al. (1998) *Nature Med* 4:285–290). One explanation is that the frequency we observed may represent a conservative estimate since it is based on events that survived through chemical selection. Observed targeting frequencies using the PAT/GFP fusion target were higher, especially when healthy freshly initiated callus was used (Table 1). While chemical selection provides a useful means for recovery of cells with the desired phenotype after targeting, some targeted cells may undergo cell cycle arrest as a result of DNA damage/repair (Elledge 1996, Kaufmann and Paules 1996), and thus may not be easily recovered as colonies when additional stress is imposed. Other factors responsible for the different frequencies may involve both experimental variances, such as method of delivery (bombardment vs. lipofection), and in vivo variances between mammalian cells and plant cells, which may include the different efficiencies for homologous pairing, strand transfer, or mismatch repair. Further studies will be needed to improve the gene conversion frequency in plant cells.

Recent advances in genomic research have generated large numbers of gene-derived DNA sequences from many organisms, including plants such as maize, rice and Arabidopsis. However, the function of the majority of genes identified by sequencing is unknown. Although candidate genes associated with specific traits can be identified by homology with sequences in other organisms, or by their expression profiles, confirmation of gene function requires reverse genetic manipulations either by transformation or mutagenesis. Currently, reverse genetics in maize and Arabidopsis is carried out mainly by screening for T-DNA or transposon insertions (McKinney et al. (1995) *Plant J.* 8:613–622), Bensen et al. (1995) *Plant Cell* 7:75–84, or potentially by gene targeting involving homologous recombination (Kempin et al. (1997) *Nature* 389:802–803). With gene targeting constructs, homologous recombination events are frequently associated with non-homologous rearrangements which can complicate interpretation (Ohl et al. (1994) *In Homologous Recombination* and *Gene Silencing in Plants*; Paszkowski J. (eds.) pp. 191–217. Kluwer Academic Publishers, Dordrecht, The Netherlands), Puchta et al. (1996) *Proc. Natl. Acad. Sci. USA* 93:5055–5060, Risseeuw et al. (1995) *Plant J.* 7:109–119). Similarly, with transposon or T-DNA disruption screens, the effects of individual insertions are frequently complicated by the presence of additional mutations, especially if these are closely linked to the gene of interest. The present study suggests that precisely controlled gene disruptions or modifications could be derived at relatively high frequencies using chimeric RNA/DNA oligonucleotides. Since chimeric oligonucleotides have no free ends (Yoon et al. (1996) *Proc. Natl. Acad. Sci. USA* 93:2071–2076), random insertion may be prevented, thereby increasing their mutational specificity. Finally, the present study indicates that it is feasible to use chimeric RNA/DNA oligonucleotides to engineer new crops with superior traits without having to introduce foreign genes.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of introducing a predetermined alteration in a target sequence of the genome of a plant cell, said method comprising:

introducing a chimeric oligonucleotide into the plant cell, said oligonucleotide having at least a first block of RNA residues and a second block of RNA residues, wherein said first and said second blocks of RNA residues are homologous to a plant nucleotide sequence and flank a block of DNA residues (DNA block), said oligonucleotide is capable of folding to form a duplex oligonucleotide; and, maintaining the chimeric oligonucleotide within the plant cell whereby the alteration is introduced into the target genomic sequence.

2. A method of introducing a predetermined alteration in a target sequence of the genome of a plant cell, said method comprising:

introducing a chimeric oligonucleotide into the plant cell, said oligonucleotide having at least a first block of RNA residues and a second block of RNA residues, wherein said first and said second blocks of RNA residues are homologous to a plant nucleotide sequence and flank a block of DNA residues (DNA block), said oligonucleotide is capable of folding to form a duplex oligonucleotide; and, wherein said oligonucleotide comprises at least one region of contiguous unpaired bases disposed so that said region of contiguous unpaired bases separates the oligonucleotide into a first and second strand; and, maintaining the chimeric oligonucleotide within the plant cell whereby the alteration is introduced into the target genomic sequence.

3. The method of claim 2, wherein said first and said second blocks of RNA residues are comprised of a 2'-O or 2'-OMe ribose.

4. The method of claim 2, wherein said first and said second blocks of RNA residues are comprise at least 5 contiguous nucleotides.

5. The method of claim 3, wherein said DNA block comprises at least 5 contiguous nucleotides.

6. The method of claim 5, wherein said plant nucleotide sequence is a nucleotide sequence that encodes a herbicide resistance gene.

7. The method of claim 6, wherein said herbicide resistance gene confers resistance to sulfonylurea.

8. The method of claim 6, wherein said herbicide resistance gene confers resistance to imidazolinone.

9. The method of claim 6, wherein said herbicide resistance gene is a 5-enol pyruvylshikimate-3-phosphate synthase gene.

10. The method of claim 6, wherein said herbicide resistance gene is acetohydroxy acid synthetase (AHAS) gene.

11. The method of claim 2, wherein the DNA block comprises at least one mismatch to the target sequence.

12. The method of claim 2, wherein the plant cell is from a dicot.

13. The method of claim 2, wherein the plant cell is from a monocot.

14. The method of claim 13, wherein the monocot is maize.

15. The method of claim 2, wherein the chimeric oligonucleotide comprises a sequence of SEQ ID NO: 1, 2, 3, 4, 5, 6, 7, 8, 9, or 10.

16. The method of claim 2, wherein the chimeric oligonucleotide comprises a sequence of SEQ ID NO:11 or 12.

17. A method of introducing a predetermined alteration in a target sequence of the genome of a plant, said method comprising:

introducing a chimeric oligonucleotide into the plant, said oligonucleotide having at least a first block of RNA residues and a second block of RNA residues, wherein said first and said second blocks of RNA residues are homologous to a plant nucleotide sequence and flank a block of DNA residues (DNA block), said oligonucleotide is capable of folding to form a duplex oligonucleotide; and, maintaining the chimeric oligonucleotide within the plant whereby the alteration is introduced into the target genomic sequence.

18. The method of claim 17, wherein said oligonucleotide comprises at least one region of contiguous unpaired bases disposed so that said region of contiguous unpaired bases separates the oligonucleotide into a first and second strand.

19. The method of claim 18, wherein said first and said second blocks of RNA residues are comprised of a 2'-O or 2'-OMe ribose.

20. The method of claim 18, wherein said first and said second blocks of RNA residues comprise at least 5 contiguous nucleotides.

21. The method of claim 19, wherein said DNA block comprises at least 5 contiguous nucleotides.

22. The method of claim 21, wherein said plant nucleotide sequence is a nucleotide sequence that encodes a herbicide resistance gene.

23. The method of claim 22, wherein said herbicide resistance gene confers resistance to sulfonylurea.

24. The method of claim 22, wherein said herbicide resistance gene confers resistance to imidazolinone.

25. The method of claim 22, wherein said herbicide resistance gene is a 5-enol pyruvylshikimate-3-phosphate synthase gene.

26. The method of claim 22, wherein said herbicide resistance gene is acetohydroxy acid synthetase (AHAS) gene.

27. The method of claim 18, wherein the DNA block comprises at least one mismatch to the target sequence.

28. The method of claim 18, wherein the plant is a dicot.

29. The method of claim 18, wherein the plant is a monocot.

30. The method of claim 29, wherein the monocot is maize.

31. The method of claim 18, wherein the chimeric oligonucleotide comprises a sequence of SEQ ID NO: 1, 2, 3, 4, 5, 6, 7, 8, 9, or 10.

32. The method of claim 18, wherein the chimeric oligonucleotide comprises a sequence of SEQ ID NO: 11 or 12.

* * * * *

UNITED STATES PATENT AND TRADEMARK OFFICE

CERTIFICATE OF CORRECTION

PATENT NO. : 6,528,700 B1 
DATED : March 4, 2003
INVENTOR(S) : Baszczynski et al.

It is certified that error appears in the above-identified patent and that said Letters Patent is hereby corrected as shown below:

Title page,
Item [56], References Cited, OTHER PUBLICATIONS, insert the following reference:
-- Boase et al., In Vitro Cellular and Development Biology, 1998, Vol. 34: 46-51 --.

Item [57], ABSTRACT,
Line 3, after “a” insert -- plant cell, wherein the oligonucleotide comprises at least two intervening blocks of --.

Column 4,
Line 10, after “the” insert -- oligonucleotide (SEQ ID NO:7) are provided. A fragment of the maize EPSPS amino --.

Column 17-18, Table 2,
Line 2, under sub-heading “Amino Acid”, “GIy” should read -- Gly --;
Line 4, under sub-heading “Nucleotide” “CCT+CAT” should read -- CCT→ CAT --.

Column 33,
Line 39, delete “are”.

Signed and Sealed this

Fifth Day of August, 2003

JAMES E. ROGAN
*Director of the United States Patent and Trademark Office*

SEQUENCE LISTING

```
<160> NUMBER OF SEQ ID NOS: 29

<210> SEQ ID NO 1
<211> LENGTH: 102
<212> TYPE: DNA
<213> ORGANISM: Zea mays
<220> FEATURE:
<221> NAME/KEY: misc_RNA
<222> LOCATION: (47)..(58)
<221> NAME/KEY: misc_RNA
<222> LOCATION: (66)..(70)
<221> NAME/KEY: misc_RNA
<222> LOCATION: (77)..(88)

<400> SEQUENCE: 1

ggggaatgct ggaatcgcaa tgcggtcctt gacagcagct gtttttacag cugcugucaa     60

ggaccgcauu gcgattccag cauuccccgc gcgttttcgc gc                        102


<210> SEQ ID NO 2
<211> LENGTH: 90
<212> TYPE: DNA
<213> ORGANISM: Zea mays
<220> FEATURE:
<221> NAME/KEY: misc_RNA
<222> LOCATION: (41)..(50)
<221> NAME/KEY: misc_RNA
<222> LOCATION: (56)..(61)
<221> NAME/KEY: misc_RNA
<222> LOCATION: (67)..(76)

<400> SEQUENCE: 2

ggaatgctgg aattgcaatg cggtcattga cagcagtttt cugcugucaa tgaccgcauu     60

gcaattccag cauuccgcgc gttttcgcgc                                      90


<210> SEQ ID NO 3
<211> LENGTH: 102
<212> TYPE: DNA
<213> ORGANISM: Zea mays
<220> FEATURE:
<221> NAME/KEY: misc_RNA
<222> LOCATION: (47)..(58)
<221> NAME/KEY: misc_RNA
<222> LOCATION: (77)..(88)

<400> SEQUENCE: 3
```

-continued

```
ggggaatgct ggaatcgcaa tgcggtcctt gacagcagct gtttttacag cugcugucaa     60

ggaccgcatt gcgattccag cauuccccgc gcgttttcgc gc                        102


<210> SEQ ID NO 4
<211> LENGTH: 90
<212> TYPE: DNA
<213> ORGANISM: Zea mays
<220> FEATURE:
<221> NAME/KEY: misc_RNA
<222> LOCATION: (41)..(50)
<221> NAME/KEY: misc_RNA
<222> LOCATION: (67)..(76)

<400> SEQUENCE: 4

ggaatgctgg aattgcaatg cggtcattga cagcagtttt cugcugucaa tgaccgcatt     60

gcaattccag cauuccgcgc gttttcgcgc                                      90


<210> SEQ ID NO 5
<211> LENGTH: 102
<212> TYPE: DNA
<213> ORGANISM: Zea mays
<220> FEATURE:
<221> NAME/KEY: misc_RNA
<222> LOCATION: (47)..(70)
<221> NAME/KEY: misc_RNA
<222> LOCATION: (77)..(88)

<400> SEQUENCE: 5

ggggaatgct ggaatcgcaa tgcggtcctt gacagcagct gtttttacag cugcugucaa     60

ggaccgcauu gcgattccag cauuccccgc gcgttttcgc gc                        102


<210> SEQ ID NO 6
<211> LENGTH: 84
<212> TYPE: DNA
<213> ORGANISM: Zea mays
<220> FEATURE:
<221> NAME/KEY: misc_RNA
<222> LOCATION: (38)..(55)
<221> NAME/KEY: misc_RNA
<222> LOCATION: (61)..(70)

<400> SEQUENCE: 6

ggaatgctgg aattgcaatg cggtcattga cagttttcug ucaaugaccg cauugcaatt     60

ccagcauucc gcgcgttttc gcgc                                            84


<210> SEQ ID NO 7
<211> LENGTH: 102
<212> TYPE: DNA
<213> ORGANISM: Zea mays
<220> FEATURE:
<221> NAME/KEY: misc_RNA
<222> LOCATION: (47)..(58)
<221> NAME/KEY: misc_RNA
<222> LOCATION: (66)..(88)

<400> SEQUENCE: 7

ggggaatgct ggaatcgcaa tgcggtcctt gacagcagct gtttttacag cugcugucaa     60

ggaccgcauu gcgauuccag cauuccccgc gcgttttcgc gc                        102


<210> SEQ ID NO 8
<211> LENGTH: 84
<212> TYPE: DNA
<213> ORGANISM: Zea mays
<220> FEATURE:
```

-continued

<221> NAME/KEY: misc_RNA
<222> LOCATION: (38)..(55)
<221> NAME/KEY: misc_RNA
<222> LOCATION: (61)..(70)

<400> SEQUENCE: 8
ggaatgctgg aattgcaatg cggtcattga cagttttcug ucaaugaccg cauugcaatt 60
ccagcauucc gcgcgttttc gcgc 84

<210> SEQ ID NO 9
<211> LENGTH: 68
<212> TYPE: DNA
<213> ORGANISM: Zea mays
<220> FEATURE:
<221> NAME/KEY: misc_RNA
<222> LOCATION: (30)..(39)
<221> NAME/KEY: misc_RNA
<222> LOCATION: (45)..(54)

<400> SEQUENCE: 9
ggaatgctgg aattgcaatg cggccttttg gccgcauugc aattccagca uuccgcgcgt 60
tttcgcgc 68

<210> SEQ ID NO 10
<211> LENGTH: 68
<212> TYPE: DNA
<213> ORGANISM: Zea mays
<220> FEATURE:
<221> NAME/KEY: misc_RNA
<222> LOCATION: (30)..(39)
<221> NAME/KEY: misc_RNA
<222> LOCATION: (45)..(54)

<400> SEQUENCE: 10
actgcaatgc ggtcattgac agcagttttc ugcugucaat gaccgcauug cagugcgcgt 60
tttcgcgc 68

<210> SEQ ID NO 11
<211> LENGTH: 70
<212> TYPE: DNA
<213> ORGANISM: Zea mays
<220> FEATURE:
<221> NAME/KEY: misc_RNA
<222> LOCATION: (31)..(40)
<221> NAME/KEY: misc_RNA
<222> LOCATION: (47)..(56)

<400> SEQUENCE: 11
ggaatgctgg aatcgcaatg cggccatttt uggccgcauu gcgattccag cauuccgcgc 60
gttttcgcgc 70

<210> SEQ ID NO 12
<211> LENGTH: 72
<212> TYPE: DNA
<213> ORGANISM: Zea mays
<220> FEATURE:
<221> NAME/KEY: misc_RNA
<222> LOCATION: (32)..(41)
<221> NAME/KEY: misc_RNA
<222> LOCATION: (49)..(58)

<400> SEQUENCE: 12
actgcaatgc ggtccttgac agcagctttt tagcugcugu caaggaccgc auugcagugc 60
gcgttttcgc gc 72

-continued

<210> SEQ ID NO 13
<211> LENGTH: 68
<212> TYPE: DNA
<213> ORGANISM: Zea mays
<220> FEATURE:
<221> NAME/KEY: misc_RNA
<222> LOCATION: (30)..(39)
<221> NAME/KEY: misc_RNA
<222> LOCATION: (45)..(54)

<400> SEQUENCE: 13
ctatgatccc taatggtggg gcttttttta aagccccacc attagggauc auaggcgcgt 60
tttcgcgc 68

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence:
oligonucleotide primer

<400> SEQUENCE: 14
cggtgacgca gatctatcca acattgtcca agggc 35

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence:
oligonucleotide primer

<400> SEQUENCE: 15
ggtgacgcag atctaggtac catcgtccaa gggcgag 37

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence:
oligonucleotide primer

<400> SEQUENCE: 16
gcagtgggac aggttctat 19

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:
oligonucleotide primer

<400> SEQUENCE: 17
agtcctgcca tcaccatcca 20

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence:
oligonucleotide primer

<400> SEQUENCE: 18

-continued acccgctccc ccgtcat 17

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence:
oligonucleotide primer

<400> SEQUENCE: 19
atctgctgct ggatgtcctt gg 22

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence:
oligonucleotide primer

<400> SEQUENCE: 20
cgcaacgcct acgactgga 19

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence:
oligonucleotide primer

<400> SEQUENCE: 21
tgatgccgtt cttctgcttg tc 22

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: polypeptide
translation of active oligonucleotide

<400> SEQUENCE: 22

Gly Asn Ala Gly Ile Ala Met Arg Ser Leu Thr Ala Ala Val
1 5 10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: polypeptide
translation of active oligonucleotide

<400> SEQUENCE: 23

Asn Ala Gly Ile Ala Met Arg Ser Leu Thr Ala
1 5 10

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: polypeptide
translation of active oligonucleotide -continued

<400> SEQUENCE: 24

Asn Ala Gly Ile Ala Met Arg Ser Leu
1 5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: polypeptide translation of active oligonucleotide

<400> SEQUENCE: 25

Asn Ala Gly Ile Ala Met Arg Pro
1 5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: polypeptide translation of active oligonucleotide

<400> SEQUENCE: 26

Thr Ala Met Arg Ser Leu Thr Ala
1 5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: polypeptide translation of active oligonucleotide

<400> SEQUENCE: 27

Met Ile Pro Asn Gly Gly Ala
1 5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: polypeptide translation of active oligonucleotide

<400> SEQUENCE: 28

Thr Gly Gln Val Ala Arg Arg Met
1 5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: polypeptide translation of active oligonucleotide

<400> SEQUENCE: 29

Thr Gln Ile Tyr Val Pro Ser Ser
1 5